US008455541B2

(12) United States Patent
Lee et al.

(10) Patent No.: US 8,455,541 B2
(45) Date of Patent: Jun. 4, 2013

(54) PHARMACEUTICAL COMPOSITION COMPRISING AN EXTRACT OF PSEUDOLYSIMACHION LONGIFOLIUM AND THE CATALPOL DERIVATIVES ISOLATED THEREFROM HAVING ANTIINFLAMMATORY, ANTIALLERGIC AND ANTIASTHMATIC ACTIVITY

(75) Inventors: Hyeong Kyu Lee, Daejeon (KR); Sei Ryang Oh, Daejeon (KR); Kyung Seop Ahn, Daejeon (KR); Sang Ku Lee, Daejeon (KR); Joong Ku Lee, Daejeon (KR); Ok Kyoung Kwon, Daejeon (KR); Doo Young Kim, Daejeon (KR); Hyouk Joung, Daejeon (KR); Gui Hua Quan, Daejeon (KR); Mi Jin Kim, Daejeon (KR); Bo Young Park, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/427,352

(22) Filed: Mar. 22, 2012

(65) Prior Publication Data
US 2012/0184499 A1 Jul. 19, 2012

Related U.S. Application Data

(62) Division of application No. 11/916,216, filed as application No. PCT/KR2006/002092 on May 30, 2006, now Pat. No. 8,168,235.

(30) Foreign Application Priority Data

| May 30, 2005 | (KR) | 10-2005-0045755 |
| May 30, 2005 | (KR) | 10-2005-0045756 |
| May 29, 2006 | (KR) | 10-2006-0048104 |
| May 29, 2006 | (KR) | 10-2006-0048319 |

(51) Int. Cl.
*A61K 31/35* (2006.01)
(52) U.S. Cl.
USPC .......................... 514/456; 514/453; 424/725
(58) Field of Classification Search
None
See application file for complete search history.

(56) References Cited

U.S. PATENT DOCUMENTS
2004/0058983 A1 3/2004 Vuorela et al.

FOREIGN PATENT DOCUMENTS

| CN | 1468601 A | 1/2004 |
| CN | 1634413 A | 7/2005 |
| CN | 1666992 A | 9/2005 |
| CN | 1698841 A | 11/2005 |
| CN | 1699392 A | 11/2005 |
| JP | 59-155314 | 9/1984 |
| JP | 10-298098 | 11/1998 |
| JP | 2001-278796 | 10/2001 |
| JP | 2003-261454 | 9/2003 |
| JP | 2004-506656 | 3/2004 |

OTHER PUBLICATIONS

Koshihara, et al., "Caffeic acid is a selective inhibitor for leukotriene biosynthesis", Biochim Biophys Acta., Jan. 17, 1984; 792(1): 92-97.
Hu, et al., "Effects of ferulle acid on allergic action", Acta Pharmaologica Sinica, Sep. 12, 1991, (5): 426-430.
Del Carmen Recio, et al., "Structural Considerations on the Iridoids as Anti-Inflammatory Agents", Planta Med., 1994, 60: 232-234.
Swiatek, et al., "Isolation and identification of some components of the *Veronica longifolia* and *Veronica scutellata* herbs", Acta Poloniae Pharmaceutica, 1980, 37(5): 567-572.
Suomi, et al., "Extraction of iridoid glycosides and their determination by micellar electorokinetic capillary chromatography", Journal of Chromatography A, 2000, 868: 73-83.
Jia, et al., "Pikuroside: A Novel Iridoid from *Picrorhiza kurroa*", J. Nat. Prod., 1999, 62: 901-903.
W. D. J. Koch, "Pseudolysimachion", Flora of China, 1998, 18: 62-65.
http://www.nhlbi.nih.gov/health/dcilDiseases/Asthma/Asthma_Prevention.html—accessed Oct. 2010.
http://plants.usda.gov/java/profile?symbol=PSL06—accessed Oct. 2010.
Qi Juia, et al., "Pikuroside: A Novel Iridoid from *Picrorhiza Kurroa*, Journal of natural Products", 1999, 62: 901-903.
Picerno, et al., "Anti-Inflammatory Activity of Verminoside from Kigelia Africana and Evaluation of Cutaneous Irritation in Cell Cultures and Reconstituted Human Epidermis", 2005, 68: 1610-1614.
Taskova, et al., "Iridoid Glucosides of the Genus Veronica s.l. And their Systematic Significance", Plant Systematics and Evolution, 2002, 231: 1-17.
Gao, et al., "Chemical constituents of *Veronica ciliate*, as a psychrophyte from Northwest China", Journal of Northwest Plants, 2003, 23(4): 633-636.

*Primary Examiner* — Susan Hoffman
(74) *Attorney, Agent, or Firm* — Lucas & Mercanti, LLP (57) ABSTRACT

The present invention relates to a composition comprising an extract of *Pseudolysimachion* genus plant, and the catalpol derivatives isolated therefrom having anti-inflammatory, anti-allergic and anti-asthmatic activity. The extract of *Pseudolysimachion* genus plant and the catalpol derivatives isolated therefrom shows potent suppressing effect on elevated IgE, IL-4 and IL-13 levels and eosinophilia in the plasma and BALF, and mucus overproduction in the lung tissues in an OVA-induced asthmatic mouse model. Therefore, it can be used as the therapeutics or functional health food for treating and preventing inflammatory, allergic and asthmatic disease.

3 Claims, 7 Drawing Sheets

PHARMACEUTICAL COMPOSITION COMPRISING AN EXTRACT OF PSEUDOLYSIMACHION LONGIFOLIUM AND THE CATALPOL DERIVATIVES ISOLATED THEREFROM HAVING ANTIINFLAMMATORY, ANTIALLERGIC AND ANTIASTHMATIC ACTIVITY

CROSS-REFERENCE TO RELATED APPLICATIONS

This application is a divisional of U.S. patent application Ser. No. 11/916,216, filed Nov. 30, 2007, now U.S. Pat. No. 8,168,235 which is a 371 of PCT/KR2006/002092, filed May 30, 2006, which claims the benefit of Korean Patent Application Nos. 10-2005-0045756, filed May 30, 2005, 10-2005-0045755, filed May 30, 2005, 10-2006-0048319, filed May 29, 2006, and 10-2006-0048104, filed May 29, 2006, the contents of each of which are incorporated herein by reference its entirety.

TECHNICAL FIELD

The present invention relates to a composition comprising an extract of *Pseudolysimachion longifolium* and the catalpol derivatives isolated therefrom having anti-inflammatory, anti-allergic and anti-asthmatic activity.

BACKGROUND ART

Asthma has been regarded as a complex syndrome occurring in the airways, which shows various disorders such as airflow obstruction, acute or chronic inflammation, airway hyper-responsiveness (AHR) and structural remodeling (Kumar R. K. *Pharmacol. Ther.*, 91, pp 93-104, 2001).

Allergic inflammation occurring in the airways has been reported to play a critical role in asthma development and the number of patients suffering from allergic asthma has been increased to about 10% of the population in the world recently. It has been reported that the number has been reached to seventeen million in America and the market scale of the medication for allergic asthma has been enlarged to 640 billion $ in America till now.

Asthma can be classified into two types, i.e., extrinsic asthma and intrinsic asthma. Extrinsic asthma caused by the exposure of antigen such as house dust mite *Dermatophagoides* as a main antigen, pollen, epithelium of animal, fungi etc shows positive reaction in skin test or bronchial provocation test against the antigen, and generally occurs in younger people. Intrinsic asthma caused by upper respiratory infection, exercise, emotional instability, cold weather, the change of humidity occurs in adult patients.

According to the aspect of pathophysiology, asthma has been recognized as a chronic inflammation occurred by following procedure; Inflammatory cells are proliferated, differentiated, and activated caused by cytokines reproducing in T-helper 2 immune cells and is moved to air way or neighboring tissue thereof. The activated inflammatory cells such as neutrophil, mast cell etc release a variety of inflammatory mediators, such as cytokines, chemokines, signaling molecules, adhesion molecules and growth factors and the structural cells in airways are involved in various stages of asthma (Elias J A et al., *J Clin Invest.*, 111, pp 291-7, 2003). In numerous studies using knockout mice models and clinical research, the critical observations in asthma could fall into several characteristic parameters, such as immune responses, eosinophilia, AHR and structural remodeling (Moffatt J D. *Pharmacol Ther* 107, pp 343-57, 2005; Spina D et al., *Trends Pharmacol Sci*, 23, pp 311-5, 2002). Each of the parameters seems not to have direct correlations with one another; however, IgE-mediated immune response and eosinophilia are prominent symptoms in the airways of allergic asthma (Bochner B. S. et al., *Annu. Rev. Immunol.*, 12, pp 295-335, 1994; Bousquet J et al., *N. Engl. J. Med.*, 323, pp 1033-9, 1990), and the produced cytokines such as IL-4, IL-5 and IL-13 in the allergic process also play an important role in AHR development and airway remodeling (Riffo-Vasquez Y et al., *Pharmacol. Ther.*, 94, pp 185-211, 2002). Indeed, asthma is a result of orchestrated inflammatory events, many of which involve specific inhibitors acting on the pathway of asthma, for example, histamine H1 antagonists, thromboxane antagonists, platelet-activating-factor antagonists, cyclooxygenase inhibitors, nitrogen monooxygenase inhibitors and prostaglandin inhibitors, have been tried but have failed in clinical trials (Moffatt J. D., *Pharmacol. Ther.*, 107, pp 343-57, 2005). In contrast, glucocorticoids, which suppress the progenitor levels of inflammatory cells to baseline by widespread inhibition of cytokine synthesis and cytokine mediated immunecell survival, has been used to manage the symptoms of asthmatic patients over a period of 30 years as far (Baatjes A. J. et al., *Pharmacol, Ther.*, 95, pp 63-72, 2002). These reports suggest that the therapeutic approach for asthma management should focus on restoring the balance of asthmatic parameters rather than searching for potent inhibitors of specific pathways of the asthmatic process.

*Pseudolysimachion longifolium* belonged to *Pseudolysimachion* genus, is a perennial herb distributed in Korea, China, Russia and Europe. Numerous species of same genus for example, *Pseudolysimachion ovutum*, *Pseudolysimachion kiusianum*, *Pseudolysimachion kiusianum* var *diamanticum*, *Pseudolysimachion kiusianum* var *villosum*, *Pseudolysimachion dahuricum*, *Pseudolysimachion pyrethrinum*, *Pseudolysimachion linarifolium*, *Pseudolysimachion linarifolium* var. *villosulum*, *Pseudolysimachion rotundum* var. *subintegrum*, *Pseudolysimachion rotundum* var. *coreanum*, *Pseudolysimachion insulare*, and *Pseudolysimachion undulata* have been reported and the plants contains mannitol, 6-hydroxyluteolin as a main ingredient (Chung B S and Shin M K, *HyangyakDaeSaJeon*, Youngrimsa, pp 913-914, 1998).

However, there has been not reported or disclosed about the suppressive effect on inflammatory, allergic and asthmatic disease of the extract from *P. longifolium* and the catalpol derivatives isolated therefrom in any of above cited literatures, the disclosures of which are incorporated herein by reference.

Accordingly, the present inventors have discovered that the extract of *P. longifolium* and the catalpol derivatives isolated therefrom show the suppressive effect on asthmatic parameters, such as IgE level, cytokine release, and eosinophilia, AR and mucus hypersecretion in OVA-sensitized/challenged mouse model and finally completed the present invention.

SUMMARY OF THE INVENTION

The present invention provides a pharmaceutical composition and a health food comprising an extract or catalpol derivatives isolated from *P. longifolium* as an active ingredient in an effective amount to treat and prevent inflammatory, allergic and asthmatic disease.

The present invention also provides a use of an extract of *P. longifolium* and the catalpol derivatives isolated therefrom showing anti-inflammatory, anti-allergic and anti-asthmatic activity.

The present invention also provides a method of treating or preventing inflammatory, allergic and asthmatic disease in a mammal comprising administering to said mammal an effective amount of an extract of *P. longifolium* and the catalpol derivatives isolated therefrom, together with a pharmaceutically acceptable carrier thereof.

DETAILED DESCRIPTION OF THE INVENTION

Accordingly, it is an object of the present invention to provide a composition comprising a crude extract or organic solvent soluble extract of *Pseudolysimachion* genus plant, as an active ingredient for the treatment and prevention of inflammatory, allergic and asthmatic disease.

The term "crude extract" disclosed herein comprises the extract prepared by extracting plant material with water, lower alcohols such as methanol, ethanol, preferably methanol and the like, or the mixtures thereof.

The term "organic solvent soluble extract" disclosed herein can be prepared by extracting the above described crude extract with organic solvent, for example, butanol, acetone, ethyl acetate, chloroform or dichloromethane, preferably butanol.

The term "*Pseudolysimachion* genus" disclosed herein comprises *P. longifolium, P. ovtum, P. kiusianum, P. kiusianum* var. *diamanticum, P. kiusianum* var. *villosum, P. dahuricum, P. pyrethrinum, P. linarifolium, P. linarifolium* var. *villosulum, P. rotundum* var. *subintegrum, P. rotundum* var. *coreanum, P. insulare* and *P. undulate*.

The present invention provides a pharmaceutical composition comprising catalpol derivatives represented by following chemical formula (I), or a pharmaceutically acceptable salt thereof as an active ingredient in an effective amount to treat and prevent inflammatory, allergic and asthma disease:

(I)

wherein,
R is independently at least one groups selected from a hydrogen atom, benzoyl or cinnamoyl group substituted with $C_1$-$C_3$ lower alkyl group or $C_1$-$C_3$ lower alkoxy group.

In the above formula (I), preferably, R group comprises 3,4-dihydroxybenzoyl, 4-hydroxy-3-methozybenzoyl, 3-hydroxy-4-methozybenzoyl, 4-hydroxybenzoyl, 3,4-dimethoxybenzoyl, 3,4-dihydroxycinnamoyl and 3-hydroxy-4-methoxycinnamoyl.

The catalpol derivatives of the present invention can be isolated from *P. longifolium* or synthesized by general procedure well known in the art (Herbert O. house., Modern Synthetic Reactions, $2^{nd}$ Ed., The Benjamin/Cummings Publishing Co., 1972).

In accordance with another aspect of the present invention, there is also provided a use of crude extract or organic solvent soluble extract of *Pseudolysimachion* genus plant, or the catalpol derivatives isolated therefrom for manufacture of medicines employed for treating or preventing inflammatory, allergic and asthmatic disease.

In accordance with another aspect of the present invention, there is also provided a method of treating or preventing inflammatory, allergic and asthmatic disease in mammals, wherein the method comprises administering a therapeutically effective amount of crude extract or organic solvent soluble extract of *Pseudolysimachion* genus plant, or the catalpol derivatives isolated therefrom into the mammal suffering with inflammatory, allergic and asthmatic disease.

An inventive extract isolated from *Pseudolysimachion* genus plant, and the catalpol derivatives isolated therefrom may be prepared in accordance with the following preferred embodiment.

Hereinafter, the present invention is described in detail.

For the present invention, for example, the dried leave of *P. longifolium* is cut into small pieces and the piece was mixed with 2 to 20-fold, preferably, 5 to 10-fold volume of polar solvent, for example, water, $C_1$-$C_4$ lower alcohol such as methanol, ethanol, butanol, or the mixtures thereof, preferably methanol; and was heated at the temperature ranging from 20 to 100° C., preferably from 20 to 50° C., for the period ranging 10 to 48 hours, preferably 20 to 30 hours, by reflux extraction with hot water, cold water extraction, ultrasonication or conventional extraction, preferably by cold water extraction; the residue was filtered and then the filtrate is dried to obtain polar solvent soluble extract thereof.

In the above crude extract prepared by above step, is suspended in water, and then is mixed with 1 to 100-fold, preferably, 1 to 5-fold volume of organic solvent butanol, acetone, ethyl acetate, chloroform or dichloromethane, preferably butanol to obtain organic solvent soluble extract of the present invention.

The above organic solvent soluble extract is further subjected to silica gel column chromatography filled with silicagel eluting with mixture solvent of chloroform:methanol with increasing the polarity by changing the mixed ratio (methanol 0-100%, step gradient) to obtain several fractions. Among the fractions, the $3^{rd}$ fraction is further subjected to repeated silica gel column chromatography using a normal phase silica column (methanol 10-50% step gradient) to obtain the catalpol derivatives of the present invention. The structure was confirmed by NMR, EI-MS and optical rotation with those reported previously (Afifi-Yazar F Ü et al., *Helv Chim Acta*, 63, pp 1905-7, 1980) and the purity of the catalpol derivatives was analyzed as more than 99.5% by HPLC system.

In accordance with another aspect of the present invention, there is provided a pharmaceutical composition comprising a crude extract and organic solvent soluble extract of *P. longifolium* or the catalpol derivatives isolated therefrom prepared by the above describe preparation method for the treatment and prevention of inflammatory, allergic and asthmatic disease as active ingredients.

In accordance with another aspect of the present invention, there is also provided a use of comprising a crude extract and organic solvent soluble extract of *P. longifolium* or the catalpol derivatives isolated therefrom prepared by the above describe preparation method for manufacture of medicines employed for treating or preventing inflammatory, allergic and asthmatic disease.

In accordance with another aspect of the present invention, there is also provided a method of treating or preventing inflammatory, allergic and asthmatic disease, wherein the method comprises administering a therapeutically effective amount of comprising a crude extract and organic solvent soluble extract of *P. longifolium* or the catalpol derivatives isolated therefrom prepared by the above describe preparation method.

The inventive compound represented by general formula (I) can be transformed into their pharmaceutically acceptable salt and solvates by the conventional method well known in the art. For the salts, acid-addition salt thereof formed by a pharmaceutically acceptable free acid thereof is useful and can be prepared by the conventional method. For example, after dissolving the compound in the excess amount of acid solution, the salts are precipitated by the water-miscible organic solvent such as methanol, ethanol, acetone or acetonitrile to prepare acid addition salt thereof and further the mixture of equivalent amount of compound and diluted acid with water or alcohol such as glycol monomethylether, can be heated and subsequently dried by evaporation or filtrated under reduced pressure to obtain dried salt form thereof.

As a free acid of above-described method, organic acid or inorganic acid can be used. For example, organic acid such as methansulfonic acid, p-toluensulfonic acid, acetic acid, trifluoroacetic acid, citric acid, maleic acid, succinic acid, oxalic acid, benzoic acid, lactic acid, glycolic acid, gluconic acid, galacturonic acid, glutamic acid, glutaric acid, glucuronic acid, aspartic acid, ascorbic acid, carbonylic acid, vanillic acid, hydroiodic acid and the like, and inorganic acid such as hydrochloric acid, phosphoric acid, sulfuric acid, nitric acid, tartaric acid and the like can be used herein.

Further, the pharmaceutically acceptable metal salt form of inventive compounds may be prepared by using base. The alkali metal or alkali-earth metal salt thereof can be prepared by the conventional method, for example, after dissolving the compound in the excess amount of alkali metal hydroxide or alkali-earth metal hydroxide solution, the insoluble salts are filtered and remaining filtrate is subjected to evaporation and drying to obtain the metal salt thereof. As a metal salt of the present invention, sodium, potassium or calcium salt are pharmaceutically suitable and the corresponding silver salt can be prepared by reacting alkali metal salt or alkali-earth metal salt with suitable silver salt such as silver nitrate.

The pharmaceutically acceptable salt of the present compound comprise all the acidic or basic salt which may be present at the compounds, if it does not indicated specifically herein. For example, the pharmaceutically acceptable salt of the present invention comprise the salt of hydroxyl group such as the sodium, calcium and potassium salt thereof; the salt of amino group such as the hydrogen bromide salt, sulfuric acid salt, hydrogen sulfuric acid salt, phosphate salt, hydrogen phosphate salt, dihydrophosphate salt, acetate salt, succinate salt, citrate salt, tartarate salt, lactate salt, mandelate salt, methanesulfonate(mesylate) salt and p-toluenesulfonate (tosylate) salt etc, which can be prepared by the conventional method well known in the art.

The inventive composition for treating and preventing inflammatory, allergic and asthmatic disease may comprises the above described extracts or compounds as 0.1-50% by weight based on the total weight of the composition.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the extract of the present invention can be formulated in the form of ointments and creams.

Pharmaceutical formulations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or compound varies depending on the condition and the weight of the subject, severity, drug form, route and period of administration, and may be chosen by those skilled in the art. However, in order to obtain desirable effects, it is generally recommended to administer at the amount ranging from 0.0001 to 100 mg/kg, preferably, 0.001 to 10 mg/kg by weight/day of the inventive extract of the present invention. The dose may be administered in single or divided into several times per day.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

It is the other object of the present invention to provide a functional health food comprising the extract or compounds isolated from *P. longifolium* together with a sitologically acceptable additive for the prevention and alleviation of inflammatory, allergic and asthmatic disease.

To develop for functional health food, examples of addable food comprising the above extracts or compounds of the present invention are various food, beverage, gum, vitamin complex, health improving food and the like, and can be used as powder, granule, tablet, chewing tablet, capsule or beverage etc.

The above described composition therein can be added to food, additive or beverage, wherein, the amount of the above described extract or compound in food or beverage may generally range from about 0.01 to 80 w/w %, preferably 0.01 to 15 w/w % of total weight of food for the health food composition and 0.02 to 5 g, preferably 0.3 to 1 g on the ratio of 100 mL of the health beverage composition.

Providing that the health beverage composition of present invention contains the above described extract or compound as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 mL of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition. Examples of addable food comprising aforementioned extract therein are various food, beverage, gum, vitamin complex, health improving food and the like.

Inventive extract of the present invention has no toxicity and adverse effect therefore they can be used with safe.

The present invention is more specifically explained by the following examples. However, it should be understood that the present invention is not limited to these examples in any manner.

BRIEF DESCRIPTION OF THE DRAWINGS

The above and other objects, features and other advantages of the present invention will more clearly understood from the following detailed description taken in conjunction with the accompanying drawings, in which.

BEST MODE FOR CARRYING OUT THE INVENTION

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Reference Example, Examples and Experimental Examples are intended to further illustrate the present invention without limiting its scope.

Example 1

Preparation of the Crude Extract of *P. longifolium*

7.9 kg of dried *P. longifolium* cut into small pieces, mixed with 50 L of methanol and the mixture was stirred at room temperature for 24 hours, extracted by cold water three times. The extract was filtered with filter paper to remove the debris. The filtrate was pooled and concentrated by rotary evaporator 55-65° C. under reduced pressure and dried with freezing dryer to obtain 950.5 g of dried crude extract of *P. longifolium*.

Example 2

Preparation of Polar Solvent and Non-Polar Solvent Soluble Extract 2-1. Preparation of Ethyl Acetate Soluble Fraction 10 L of distilled water was added to 425 g of the crude extract obtained in Example 1. 10 L of ethyl acetate was added thereto in separatory funnel and shaken vigorously to divide into ethyl acetate soluble layer and water soluble layer.

Above ethyl acetate soluble layer was concentrated by rotary evaporator, dried with freeze dryer to obtain ethyl acetate soluble extract.

2-2. Preparation of Butanol/Water Soluble Fraction

Water soluble layer was fractionated by mixing with 10 L of butanol and finally, 144.0 g of n-butanol soluble extract and water soluble extract were obtained to use as a sample in the following experiments.

Example 3

Preparation of Catalpol Derivatives from the Extract of *P. longifolium*

3-1. Preparation of verproside (6-O-3,4-Dihydroxybenzoyl catalpol)

144.0 g of n-butanol soluble fraction was subjected to a silica gel column chromatography (70-230 mesh, 8.5×65 cm) and eluted with a chloroform-methanol mixture (methanol 0-100%, step gradient) to obtain five fractions. 29.1 g of fraction 2 (between chloroform-methanol 7/3-6/4, v/v) was subjected to repeated column chromatography using a normal phase silica column chromatography (silica gel, 230-400 mesh, 6.0×60 cm, chloroform-methanol mixture, methanol 10-50% step gradient). The fractions 2-4 was performed to recrystallization in methanol to obtain 14.2 g of verproside, i.e., 6-O-3,4-Dihydroxybenzoyl catalpol. The structure was confirmed by NMR ($^1$H, $^{13}$C, DEPT, HMQC, HMBC), EI-MS and optical rotation with those reported previously (Afifi-Yazar F Ü et al., *Helv Chim Acta*, 63, pp 1905-7, 1980) and the purity of verproside was analyzed as more than 99.5% by HPLC system (Shimadzu SCL-10A with SPD-M 10A vp PDA detector, column; Phenomenex Synergi 4 um Fusion RP-80, 4.6×150 mm, elution: MeOH/DW, 35/65, v/v, 0.8 ml/min).

6-O-3,4-Dihydroxybenzoyl catalpol (verproside)

$^1$H NMR (400 MHz, DMSO-$d_6$) δ: 2.47 (1H, dd, J=8.0, 9.2 Hz, H-9), 2.59 (1H, dddd, J=1.6, 4.0, 8.0, 8.0, H-5), 3.00 (1H, m, H-G4), 3.05 (1H, m, H-G2), 3.14 (1H, m, H-G5), 3.18 (1H, m, H-G3), 3.42, 3.71 (2H, m, H-G6). 3.67 (1H, s, H-7), 3.71, 3.91 (2H, d, J=13.2 Hz, each, H-10), 4.61 (1H, d, J=7.6 Hz, H-G1), 4.94 (1H, dd, J=4.0, 6.0 Hz, H-4), 5.03 (1H, d, J=8.0 Hz, H-6), 5.09 (1H, d, J=9.2 Hz, H-1), 6.41 (1H, dd, J=1.6, 6.0 Hz, H-3), 6.82 (1H, d, J=8.0 Hz, H-5'), 7.35 (1H, dd, J=2.0, 8.0 Hz, H-6'), 7.39 (1H, d, J=2.0 Hz, H-2').

$^{13}$C-NMR (100 MHz, DMSO-$d_6$) δ: 93.0 (C-1), 141.1 (C-3), 101.8 (C-4), 35.2 (C-5), 79.5 (C-6), 58.2 (C-7), 65.8 (C-8), 41.8 (C-9), 120.0 (C-1'), 116.4 (C-2'), 145.1 (C-3'), 150.8 (C-4'), 115.4 (C-5'), 122.6 (C-6'), 165.6 (C-7'), 97.9 (C-G1), 73.4 (C-G2), 76.4 (C-G3), 70.3 (C-G4), 77.5 (C-G5), 61.4 (C-G6).

3-2. Preparation of Isovanillyl Catalpol from the Extract of *P. longifolium*

17.3 g of fraction 3 was subjected to column chromatography using a normal phase silica column (silica gel, 230-400 mesh, 6.0×60 cm, chloroform-methanol mixture, methanol 10-50% step gradient). 8.5 g of fraction 3-3 was performed to recrystallization in methanol to obtain 7.2 g of isovanillyl catalpol, i.e., 6-O-3-hydroxy-4-methoxybenzoly catalpol.

6-O-3-hydroxy-4-methoxybenzoly catalpol (isovanillyl catalpol)

$^1$H-NMR (400 MHz, DMSO-$d_6$) δ: 2.47 (1H, m, H-9), 2.55 (1H, m H-5), 3.00 (1H, m, H-G4), 3.05 (1H, m, H-G2), 3.14 (1H, m, H-G5), 3.18 (1H, m, H-G3), 3.43, 3.70 (2H, m, H-G6), 3.70 (1H, br s, H-7), 3.72, 3.92 (2H, d, J=13.2 Hz, each, H-10), 4.62 (1H, d, J=8.0 Hz, H-G1), 4.95 (1H, dd, J=4.4, 6.0 Hz, H-4), 5.06 (1H, d, J=8.0 Hz, H-6), 5.11 (1H, d, J=9.2 Hz, H-1), 6.42 (1H, d, J=6.0 Hz, H-3), 7.04 (1H, d, J=8.4 Hz, H-5'), 7.42 (1H, br s, H-2'), 7.48 (1H, d, J=8.4 Hz, H-6'), 3.84 (3H, s, 4'-O—CH$_3$).

$^{13}$C-NMR (100 MHz, DMSO-$d_6$) δ: 93.0 (C-1), 141.0 (C-3), 101.6 (C-4), 35.2 (C-5), 79.7 (C-6), 58.2 (C-7), 65.8 (C-8), 41.8 (C-9), 58.4 (C-10), 121.7 (C-1'), 115.7 (C-2'), 146.3 (C-3'), 152.1 (C-4'), 111.4 (C-5'), 121.3 (C-6'), 165.3 (C-7'), 97.8 (C-G1), 73.4 (C-G2), 76.4 (C-G3), 70.3 (C-G4), 77.4 (C-G5), 61.4 (C-G6), 55.7 (4'-OCH$_3$).

3-3. Preparation of PicrosideII and Verminoside from the Extract of *P. longifolium*

1.5 g of fraction 3-5 was subjected to reversed phase silica gel column (RP-18, YMC Gel ODS-A, 6.0×60 cm, methanol/water, 1/4, v/v), subjected to sepadex LH-20 column chromatography (methanol/water, 85/15, v/v) to obtain 101.0 mg of picrosideII, i.e., 6-O-4-hydroxy-3-methozybenzoyl and 30.0 mg of verminoside, i.e., 6-O-3,4-dihydroxycinnamoyl catalpol.

6-O-4-hydroxy-3-methozybenzoyl (picrosideII)

$^1$H-NMR (400 MHz, DMSO-$d_6$) δ: 2.47 (1H, dd, J=8.0, 9.6 Hz, H-9), 2.58 (1H, dddd, J=1.2, 6.0, 8.0, 8.4 Hz, H-5), 3.00 (1H, m, H-G4), 3.05 (1H, m, H-G2), 3.14 (1H, m, H-G5), 3.18 (1H, m, H-G3), 3.42, 3.71 (2H, m, H-G6), 3.67 (1H, br s, H-7), 3.72, 3.92 (2H, d, J=13.2, each, H-10), 4.62 (1H, d, J=7.6 Hz, H-G1), 4.99 (1H, dd, J=4.4, 6.0 Hz, H-4), 5.06 (1H, d, J=8.4 Hz, H-6), 5.11 (1H, d, J=9.6 Hz, H-1), 6.42 (1H, dd, J=1.2, 6.0 Hz, H-3), 6.89 (1H, d, J=8.4 Hz, H-5'), 7.46 (1H, d, J=2.0 Hz, H-2'), 7.52 (1H, dd, J=2.0, 8.4 Hz, H-6'), 3.83 (3H, s, 3'-O—CH$_3$).

$^{13}$C-NMR (100 MHz, DMSO-$d_6$) δ: 93.0 (C-1), 141.1 (C-3), 101.8 (C-4), 35.2 (C-5), 79.7 (C-6), 58.2 (C-7), 65.8 (C-8), 41.8 (C-9), 58.5 (C-10), 120.0 (C-1'), 112.7 (C-2'), 147.5 (C-3'), 152.0 (C-4'), 115.3 (C-5'), 123.8 (C-6'), 165.6 (C-7'), 97.9 (C-G1), 73.4 (C-G2), 76.4 (C-G3), 70.3 (C-G4), 77.5 (C-G5), 61.4 (C-G6), 55.7 (3'-OCH$_3$).

6-O-3,4-dihydroxycinnamoyl catalpol (verminoside)

$^1$H-NMR (400 MHz, DMSO-$d_6$) δ: 2.43 (1H, m, H-9), 2.45 (1H, m, H-5), 3.01 (1H, m, H-G4), 3.05 (1H, m, H-G2), 3.14 (1H, m, H-G5), 3.18 (1H, m, H-G3), 3.42, 3.70 (2H, m, H-G6), 3.64 (1H, br s, H-7), 3.71, 3.90 (2H, d, J=13.2 Hz, each, H-10), 4.61 (1H, d, J=8.4 Hz, H-G1), 4.94 (1H, dd, J=4.0, 5.6 Hz, H-4), 4.99 (1H, d, J=7.2 Hz, H-6), 5.08 (1H, d, J=9.2 Hz, H-1), 6.42 (1H, d, J=5.6 Hz, H-3), 6.77 (1H, d, J=8.0 Hz, H-5'), 7.08 (1H, d, J=1.6 Hz, H-2'), 7.05 (1H, dd, J=1.6, 8.0 Hz, H-6').

$^{13}$C-NMR (100 MHz, DMSO-$d_6$) δ: 92.9 (C-1), 141.1 (C-3), 101.7 (C-4), 35.1 (C-5), 79.2 (C-6), 58.2 (C-7), 65.7 (C-8), 41.8 (C-9), 58.5 (C-10), 125.4 (C-1'), 115.8 (C-2'), 146.0 (C-3'), 148.6 (C-4'), 113.3 (C-5'), 121.6 (C-6'), 145.6 (C-7'), 115.0 (C-8'), 97.9 (C-G1), 73.4 (C-G2), 76.4 (C-G3), 70.3 (C-G4), 77.5 (C-G5), 61.4 (C-G6).

3-4. Preparation of 6-O-veratroyl Catalpol from the Extract of *P. longifolium*

6.2 g of fraction 4 was subjected to column chromatography. 1.2 g of fraction 4-3 was performed to recrystallization in methanol to obtain 672.6 mg of 6-O-veratroyl catalpol, i.e., 6-O-3,4-Dimethoxybenzoyl.

6-O-(3,4-dimethoxybenzoyl) catalpol (6-O-veratroyl catalpol)

$^1$H-NMR (400 MHz, DMSO-$d_6$) δ: 2.47 (1H, dd, J=8.0, 9.6 Hz, H-9), 2.59 (1H, dddd, J=1.6, 4.8, 8.0, 8.0 Hz, H-5), 3.00 (1H, m, H-G4), 3.05 (1H, m, H-G2), 3.14 (1H, m, H-G5), 3.18 (1H, m, H-G3), 3.42, 3.71 (2H, m, H-G6), 3.70 (1H, br s, H-7), 3.72, 3.90 (2H, d, J=13.2 Hz, each, H-10), 4.61 (1H, d, J=7.6 Hz, H-G1), 4.97 (1H, dd, J=4.8, 6.0 Hz, H-4), 5.08 (1H, d, J=8.8 Hz, H-6), 5.10 (1H, d, J=9.6 Hz, H-1), 6.42 (1H, dd, J=1.6, 6.0 Hz, H-3), 7.09 (1H, d, J=8.4 Hz, H-5'), 7.46 (1H, d, J=2.0 Hz, H-2'), 7.64 (1H, dd, J=2.0, 8.4 Hz, H-6'), 3.81, 3.84 (6H, s each, 3',4'-OCH$_3$).

$^{13}$C-NMR (100 MHz, DMSO-$d_6$) δ: 92.9 (C-1), 141.1 (C-3), 101.8 (C-4), 35.2 (C-5), 79.9 (C-6), 58.2 (C-7), 65.9 (C-8), 41.8 (C-9), 58.4 (C-10), 121.3 (C-1'), 111.8 (C-2'), 148.5 (C-3'), 153.2 (C-4'), 111.2 (C-5'), 123.5 (C-6'), 165.5 (C-7'), 97.8 (C-G1), 73.4 (C-G2), 76.4 (C-G3), 70.3 (C-G4), 77.5 (C-G5), 61.4 (C-G6), 55.6, 55.7 (3',4'-OCH$_3$).

3-5. Preparation of Minecoside from the Extract of *P. longifolium*

261.0 mg of fraction 4-4 and 288.0 mg of fraction 4-5 were subjected to repeated silica gel column chromatography (chloroform-methanol mixture, methanol 10-20% step gradient) to obtain 52.5 mg of minecoside, i.e., 6-O-3-hydroxy-4-methozycinnamoyl catalpol.

6-O-3-hydroxy-4-methoxycinnamoyl catalpol (minecoside)

$^{1}$H-NMR (400 MHz, DMSO-d$_6$) δ: 2.46 (1H, m, H-9), 2.48 (1H, m, H-5), 3.00 (1H, m, H-G4), 3.05 (1H, m, H-G2), 3.14 (1H, m, H-G5), 3.18 (1H, m, H-G3), 3.42, 3.70 (2H, m, H-G6), 3.67 (1H, br s, H-7), 3.72, 3.91 (2H, d, J=13.2 Hz, each, H-10), 4.61 (1H, d, J=8.8 Hz, H-G1), 4.94 (1H, dd, J=4.0, 6.0 Hz, H-4), 5.00 (1H, d, J=7.2 Hz, H-6), 5.09 (1H, d, J=9.2 Hz, H-1), 6.42 (1H, dd, J=1.2, 5.6 Hz, H-3), 6.96 (1H, d, J=8.0 Hz, H-5'), 7.13 (1H, d, J=2.0 Hz, H-2'), 7.17 (1H, dd, J=2.0, 8.0 Hz, H-6'), 3.82 (3H, s, —OCH$_3$).

$^{13}$C-NMR (100 MHz, DMSO-d$_6$) δ: 93.0 (C-1), 141.1 (C-3), 101.7 (C-4), 35.1 (C-5), 79.3 (C-6), 58.2 (C-7), 65.7 (C-8), 41.8 (C-9), 58.5 (C-10), 126.8 (C-1'), 114.5 (C-2'), 146.7 (C-3'), 150.2 (C-4'), 112.0 (C-5'), 121.4 (C-6'), 145.7 (C-7'), 114.5 (C-8'), 97.9 (C-G1), 73.4 (C-G2), 76.4 (C-G3), 70.3 (C-G4), 77.5 (C-G5), 61.4 (C-G6), 55.6 (4'-OCH$_3$).

3-6. Preparation of Catalpol from the Extract of *P. longifolium*

Verproside was hydrolyzed to yielded catalpol (compound I) with 0.1N of KOH. The solution was stirred for 8 hours at room temperature and neutralized with 0.1N of HCL solution. The product was concentrated by rotary evaporator under reduced pressure, subjected to reversed phase silica gel column (RP18, methanol/water, 1/4, v/v), and yielded 54.0 mg of catalpol.

Catalpol $^{1}$H-NMR (400 MHz, DMSO-d$_6$) δ: 2.12 (1H, dddd, J=1.6, 4.0, 8.0, 8.0 Hz, H-5), 2.31 (1H, d, J=8.0, 9.6 Hz, H-9), 3.00 (1H, m, H-G4), 3.05 (1H, m, H-G2), 3.11 (1H, m, H-G5), 3.17 (1H, m, H-G3), 3.34 (1H, br s, H-7), 3.40, 3.70 (2H, m, H-G6), 3.63, 3.87 (2H, d, J=12.8, each, H-10), 3.76 (1H, d, J=8.0 Hz, H-6), 4.59 (1H, d, J=8.0 Hz, H-G1), 4.90 (1H, d, J=9.6 Hz, H-1), 5.01 (1H, dd, J=4.6, 6.0 Hz, H-4), 6.36 (1H, dd, J=1.6, 6.0 Hz, H-3).

$^{13}$C-NMR (100 MHz, DMSO-d$_6$) δ: 93.2 (C-1), 140.2 (C-3), 103.3 (C-4), 37.4 (C-5), 77.1 (C-6), 60.7 (C-7), 64.8 (C-8), 42.1 (C-9), 58.9 (C-10), 97.8 (C-G1), 73.4 (C-G2), 76.4 (C-G3), 70.2 (C-G4), 77.4 (C-G5), 61.3 (C-G6).

Experimental Example 1

MTT Assay

To investigate the cytotoxic effect of inventive extract of *P. longifolium* extract and the compound isolated therefrom was determined by (3-[4,5-dimethylthiazol-2-yl]-2,5-diphenyl tetrazolium bromide (MTT) assay method (Wang Z et al., *Biol., Pharm. Bull.*, 24, pp 159-162, 2001).

Promyelotic HL-60 cells (HL-18103, 5×10$^5$ cells/ml) were seeded in 96-well plates under NGF-free condition. After 24 hours incubation, the cells were treated with the mixture of samples dissolved in 10 μl of DMSO and 10 μl of MTT solution (5 mg/ml), and incubated for 4 hours under similar condition. 4 hours later, MTT was removed and 100 μl of DMSO was dropped into each well to dissolve crystals. At 570 nm, UV absorbance was measured by microplate reader (BIO-RAD, U.S.A.) to calculate the cell viability.

As shown in Table 1, the result demonstrates that the cell viability ranges from 98% to 116% in 50 μM, from 95% to 114% in 100 μM. It is confirmed that an inventive extract or compound the present invention has no cell toxicity.

TABLE 1

Effect of compounds isolated from *P. longifolium* on HL-60 cells.

| Sample | Cell viability (%) | |
|---|---|---|
| | 50 μM | 100 μM |
| Verposide | 105 | 102 |
| 6-O-veratroyl catalpol | 116 | 114 |
| Minecoside | 98 | 95 |

Experimental Example 2

Airway Hyperresponsiveness (AHR)

Figure 1:
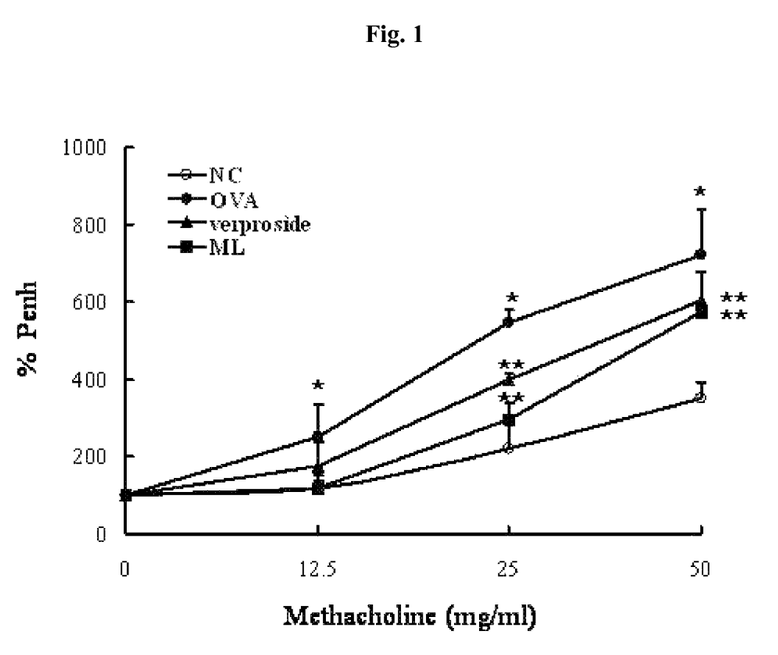
FIG. 1 presents the effects of verproside isolated from *P. longifolium* on airway hyperresponsiveness (AHR) in the ovalbumin (OVA) and methacholine challenged cells compared to montelukast (ML).

The AHR was evaluated by calculation Penh values (enhanced pause) 24 hours after the final OVA challenge. The Penh value of the OVA-treated group was significantly higher than that of the PBS control group. In the *P. longifolium* extract+OVA-challenged group, the Penh value was significantly reduced compared with that of the OVA-treated group at 30 mg/ml methacholine. (table 2) In the verproside+OVA-challenged group, the Penh value was significantly reduced compared with that of the OVA-treated group (P<0.05) A positive control, montelukast (ML), which has been widely used as an anti-asthmatic drug, showed a similar decrease of AHR with verproside (FIG. 1).

TABLE 2

Effect of *P. longifolium* extract on airway hyperresponsiveness (AHR)

| methacholine | Penh value | | | |
|---|---|---|---|---|
| (mg/ml) | 0 | 5 | 10 | 30* |
| OVA-challenged group | 0.66 ± 0.23 | 1.79 ± 0.47 | 2.75 ± 0.91 | 4.59 ± 1.07 |
| OVA + *P. longifolium* extract (% inhibition) | 0.65 ± 0.18 (—) | 1.33 ± 0.53 (25.7%) | 2.46 ± 0.26 (10.5%) | 2.85 ± 0.72* (38.0%) |

*significant difference from OVA-treated group p < 0.05

Experimental Example 3

Effect of *P. longifolium* on Ova-Induced Eosinophilia in BALF 3-1. Animal Sensitization and Airway Challenge Specific pathogen-free female BALB/c mice aged 8-10 weeks, which were routinely screened serologically for relevant respiratory pathogens, were purchased from ORIENT Co Ltd (Seoul, Korea).

Following treatment: (1) sham-sensitization plus challenge with phosphate-buffered saline (PBS; ipNeb); (2) sensitization plus challenge with OVA (ovalbumin: Sigma A5503; Sigma, St. Louis, Mo.) (ipNeb); (3) sensitization with OVA (i.p.) plus challenge with OVA (Neb) and samples (extract of *P. longifolium* or montelukast) was performed to Group of mice (n=5). Briefly, mice were sensitized by intraperitoneal injection of 20 μg OVA, which was emulsified with 2 mg aluminum hydroxide in 100 μl of PBS buffer (pH 7.4) on days 0 and 14. The mice were challenged through the airways with OVA (1% in PBS) for 20 min using an ultrasonic nubuilizer (NE-U12; Omron Corp., Tokyo, Japan) on days 28, 29 and 30 after the initial sensitization. The mice were sacrificed 48 h after the last challenge (day 32) to determine the suppression effect of extract of *P. longifolium* or verproside on the airways of allergic asthma.

3-2. Sample Treatment

The extract of *P. longifolium*, and verproside were suspended in PBS and administered intragastrically using a 25-gauge stainless steel blunt feeding needle 1 h before each challenge, and control animals were exposed only on the PBS solution. As a positive control, montelukast (MSD Korea Ltd., Seoul, Korea) was treated with the same procedure in the experiment.

The mice were sacrificed with an overdose of pentobarbital (Sigma P3761) 24 h after the last challenge, and a tracheotomy was performed. After ice-cold 0.5 ml of PBS was instilled into the lungs, bronchoalveolar lavage fluid (BALF) was obtained by aspiration three times (total 1.5 ml) via tracheal cannulation (Yamazaki T, *J. Jap. Bot.*, 43, pp 117-24, 1968)

3-3. Inflammatory Cell Counts in Bronchoalveolar Lavage Fluid

The total inflammatory cell number was assessed by counting cells in at least five squares of a hemocytometer after excluding dead cells confirmed by staining with trypan blue (Daigle I. et al., *Swiss Med Wkly*, 131, pp 231-7, 2001). 100 µl of BALF was loaded onto a slide and centrifuged (200×g, 4° C., 10 min) to fix the cells onto the slide using a cytospine machine (Hanil Science Industrial, Korea). The cells were stained by Diff-Quick® Stain reagents (Sysmex, Cat No. 38721, Switzerland) according to the manufacturer's instructions. Statistical significance was determined by Student's two-tailed t-test for independent means and the critical level for significance was set at $P<0.05$.

Figure 2:
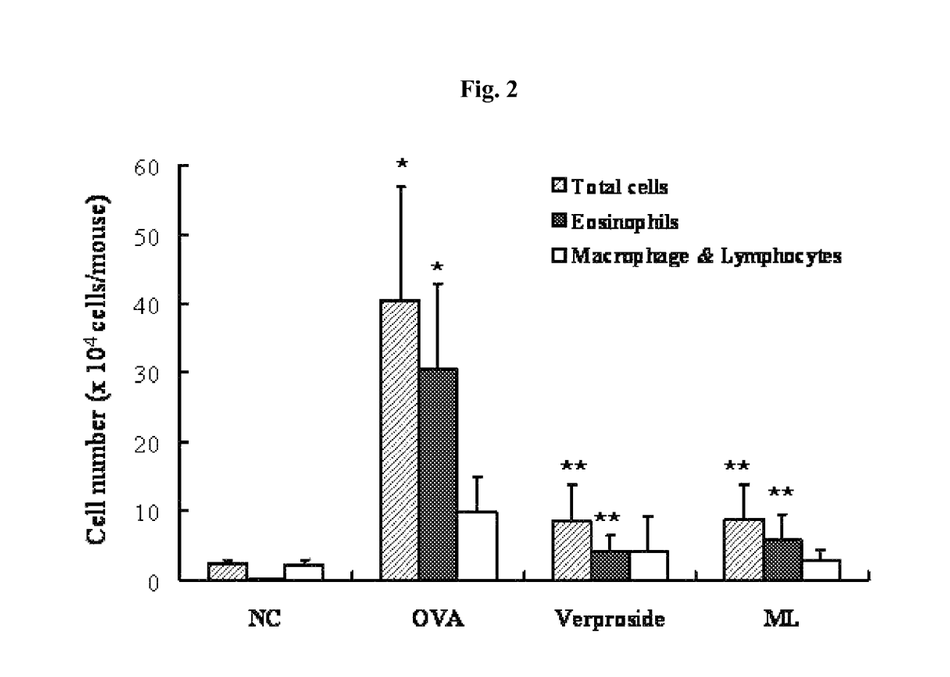
FIG. 2 presents the effects of verproside isolated from *P. longifolium* on OVA-Induced Eosinophilia in BALF in the ovalbumin (OVA) challenged mice compared to montelukast (ML).

To evaluate the suppression of verproside on the eosinophilia in OVA-challenged mice, the recruited cells in BALF were counted 48 hours after the last challenge. OVA caused a marked influx of leucocytes into the BALF from a PBS control group. As shown in FIG. 2, the total cells were counted as $40.5\pm16.4\times10^4$ cells/mouse ($P<0.001$) compared with the PBS-treated control ($2.3\pm0.6\times10^4$ cells/mouse). Eosinophils were found to be less than 5% of total cells in the PBS-treated mice, however, these were increased dramatically to be more than 75% of total leukocytes in the BALF of OVA-challenged mice. In the verproside-treated mice, the cell migration was significantly attenuated; 79.3±13.1% decrease in total cells ($P<0.005$) and 86.2±7.2% in eosinophils ($P<0.001$) from a OVA-treated control group. A positive control, montelukast (ML), showed a similar suppressive effect of leukocyte influx in BALF as 78.3±12.1% decrease in total cells ($P<0.005$) and 80.7±11.1% decrease in eosinophils ($P<0.005$) (FIG. 2). In the treatment of *P. longifolium* extract+OVA, the recruitments of cells were significantly attenuated also; 66.0±13.2% decrease in total cells and 75.8±7.6% decrease in eosinophils, respectively.

Experimental Example 4

Lung Histology

Figure 3:
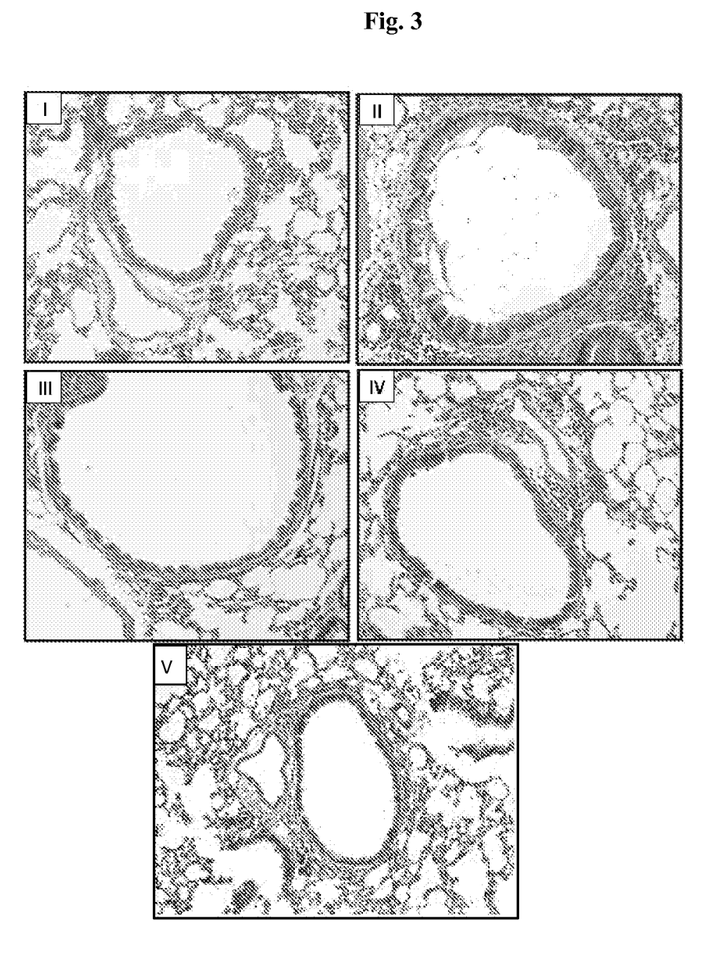
FIG. 3 presents the effects of verproside isolated from *P. longifolium* and *P. longifolium* extract on eosinophilia by the lung tissues stained with hematoxylin (I: Normal Control; II: OVA-challenged mice; III: OVA challenge+verproside treated mice; IV: OVA challenge+Montelukast treated; V: OVA challenged+*P. longifolium* extract-treated mice).

To estimate the suppressive effect of verproside on the eosinophilia, lung tissues were collected 48 hours after the last challenge. The lung tissue was fixed for 24 h in 10% neutral-buffered formalin. After being embedded in paraffin, it is sliced into 4-µm thickness of sections and the tissue was stained with H&E solution (hematoxylin; Sigma MHS-16 and eosin, Sigma HT110-1-32). In the OVA-challenged mice, leukocytes were found to be infiltrated into the peri-bronchiole and peri-vascular connective tissue; of these leukocytes, eosinophilia was mainly observed (FIG. 3-II, $P<0.005$). In the verproside+OVA-challenged mice, the infiltration of eosinophil-rich leukocytes was significantly attenuated compared with the OVA-treated mice (FIG. 3-III, $P<0.05$). The suppressive effect of Montelukast (ML) was shown similar with that of verproside (FIG. 3-IV, $P<0.05$). In the treatment of *P. longifolium* extract+OVA, the suppressive effect of leukocyte infiltration was found clearly (FIG. 3-V).

Figure 4:
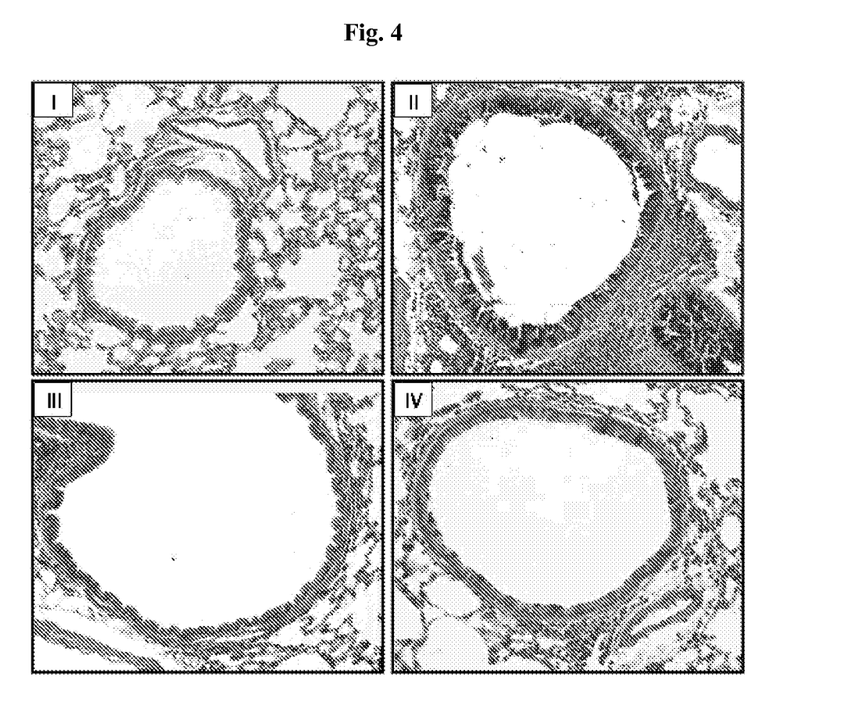
FIG. 4 presents the effects of verproside isolated from *P. longifolium* on eosinophilia by the lung tissues stained in Periodic Acid Schiff (PAS) staining (I: Normal Control; II: OVA-challenged mice; III: OVA challenge+verproside treated mice; IV: OVA challenge+Montelukast treated).
Figure 5:
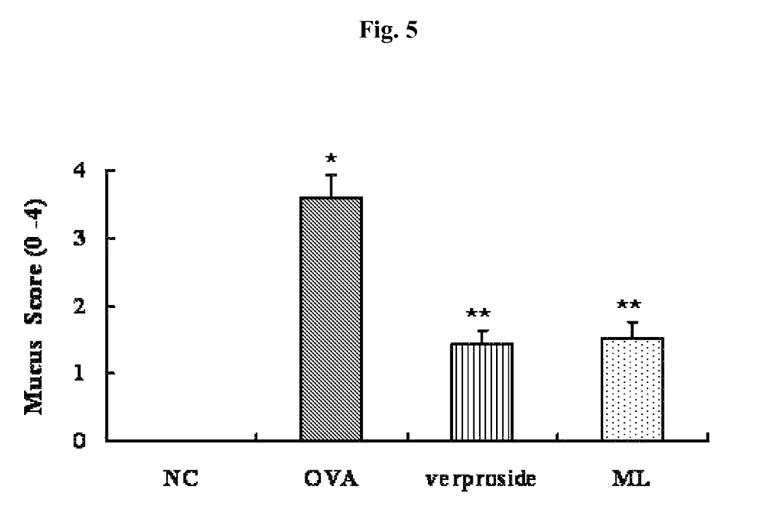
FIG. 5 presents the effects of verproside isolated from *P. longifolium* on mucus hypersecretion in the bronchial airways (NC: Normal Control; OVA: OVA-challenged mice; verproside: OVA challenge+verproside treated mice; ML: OVA challenged+Montelukast treated).

In Periodic acid Schiff (PAS) staining, mucus overproduction in the OVA-treated mice was clearly observed as a violet color in the bronchial airways compared with the normal mice. In contrast, mucus was markedly diminished in the verproside+OVA-challenged mice (FIG. 4). Goblet-cell hyperplasia in the airway epithelium was quantified based on a five-point system: 0, no goblet cells; 1, <25% of the epithelium; 2, 25-50% of the epithelium; 3, 50-75% of the epithelium; 4, >75% of the epithelium. For each mouse, five airway sections that were randomly distributed throughout the left lung were analysed, and their average scores were calculated. Quantitative analysis of mucus production was performed using an image analyzer (Leica Microsystem Imaging solution Ltd.; Cambridge, UK). As shown in FIG. 5, the mucus area was scored as 3.60±0.64 in the OVA-treated mice compare with PBS-treated mice ($P<0.05$) and it was significantly decreased to 1.43±0.23 in the verproside+OVA-treated mice ($P<0.05$), which was even lower than the positive reference, montelukast (1.53±0.24, $P<0.05$).

These results demonstrated that verproside reduced eosinophilia and mucus hypersecretion significantly in the airway remodeling process.

Experimental Example 5

Measurement of IgE and Cytokines

Complementary capture and detection antibody pairs for mouse IgE antibodies were purchased from PharMingen (San Diego, Calif.), and the IgE enzyme-linked immunosorbent assay (ELISA) was performed according to the manufacturer's directions. Duplicate samples in plasma were diluted to 1:100. IgE levels in each sample were measured from optical density readings at 450 nm, and IgE concentrations were calculated from a standard curve that was generated using recombinant IgE (5-2,000 ng/ml). The amount of IL-4 and IL-13 contained in BALF was measured with a specific mouse ELISA kit (R&D Systems; Minneapolis, Minn.). The detection limit of the assays was 250 pg/ml.

Figure 6:
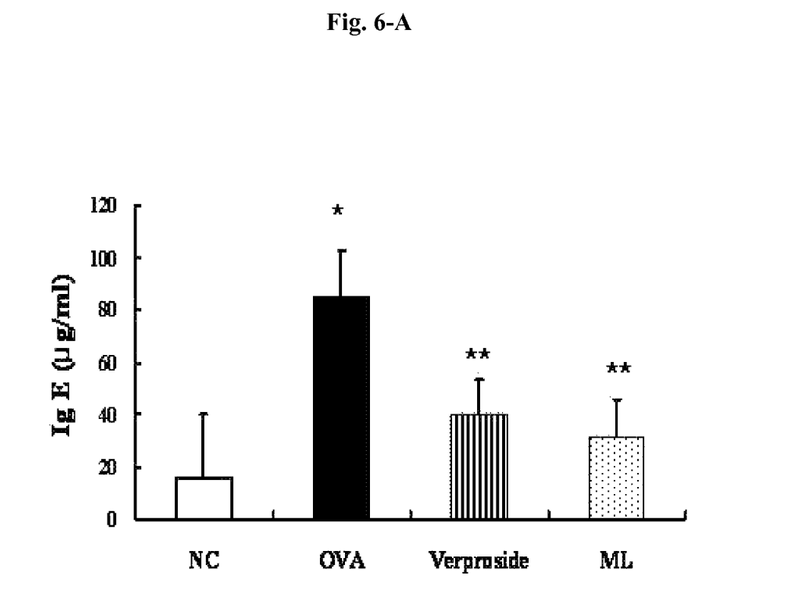
FIG. 6 presents the effects of verproside isolated from *P. longifolium* on IgE levels and cytokines, IL-4 and IL-3, concentrations in BALF of the asthmatic model compared to montelukast (NC: Normal Control; OVA: OVA-challenged mice; Verproside: OVA challenge+verproside treated mice; ML: OVA challenged+Montelukast treated).

As shown in FIG. 6-A and 6-B, The IgE levels were found to be greatly increased in the OVA-treated mice: 85.6±17.3 µg/ml (plasma, $P<0.05$) and 59.4±38.4 (BALF, $P<0.005$) compared with the PBS-treated mice (16.9±23.9 µg/ml in plasma, 1.0±0.1 ng/ml in BALF). The IgE levels of verproside-treated mice were significantly reduced to 40.2±13.2 µg/ml (plasma, $P<0.005$) and 21.5±11.2 ng/ml (BALF, $P<0.05$). In the case of montelukast, the IgE levels were much lower as 31.4±14.2 µg/ml (plasma, $P<0.005$) and 3.8±0.7 ng/ml (BALF, $P<0.05$)

To determine the effect of verproside on cytokine release in the OVA-induced asthmatic mice, the levels of cytokines (IL-4 and IL-13) in BALF were measured using ELISA 48 hours after the last challenge. OVA challenge induced a significant elevation of the cytokines to 14.1±6.1 pg/ml (IL-4) and 178.5±96.4 pg/ml (IL-13) in the BALF compared with the control (IL-4, 0.1±0.5 pg/ml; IL-13, 0.1±1.0 pg/ml). In the verproside-treated group, the cytokines were significantly suppressed; 64.5±27.7% decrease in IL-4 ($P<0.05$) and 74.9±15.5% in IL-13 ($P<0.005$) from a OVA-challenged group. Montelukast also showed a significant reduction in both of IL-4 (69.5±22.0% decrease, P<0.05) and IL-13 (84.5±8.2% decrease, P<0.05) from the control. These results demonstrate that verproside reduced the IL-4 and IL-13 concentrations in the BALF of the asthmatic model as montelukast did (FIG. 6-C and 6-D).

Hereinafter, the formulating methods and kinds of excipients will be described, but the present invention is not limited to them. The representative preparation examples were described as follows.

Preparation of Injection

| | |
|---|---|
| Dried powder of Example 1 or verproside | 100 mg |
| Sodium metabisulfite | 3.0 mg |
| Methyl paraben | 0.8 mg |
| Propyl paraben | 0.1 mg |
| Distilled water for injection | optimum amount |

Injection preparation was prepared by dissolving active component, controlling pH to about 7.5 and then filling all the components in 2 mL ample and sterilizing by conventional injection preparation method.

Preparation of Powder

| | |
|---|---|
| Dried powder of Example 1 or verproside | 500 mg |
| Corn Starch | 100 mg |
| Lactose | 100 mg |
| Talc | 10 mg |

Powder preparation was prepared by mixing above components and filling sealed package.

Preparation of Tablet

| | |
|---|---|
| Dried powder of Example 1 or verproside | 200 mg |
| Corn Starch | 100 mg |
| Lactose | 100 mg |
| Magnesium stearate | optimum amount |

Tablet preparation was prepared by mixing above components and entabletting.

Preparation of Capsule

| | |
|---|---|
| Dried powder of Example 1 or verproside | 100 mg |
| Lactose | 50 mg |
| Corn starch | 50 mg |
| Talc | 2 mg |
| Magnesium stearate | optimum amount |

Tablet preparation was prepared by mixing above components and filling gelatin capsule by conventional gelatin preparation method.

Preparation of Liquid

| | |
|---|---|
| Dried powder of Example 1 or verproside | 1000 mg |
| Sugar | 20 g |
| Polysaccharide | 20 g |
| Lemon flavor | 20 g |

Liquid preparation was prepared by dissolving active component, and then filling all the components in 1000 mL ample and sterilizing by conventional liquid preparation method.

Preparation of Health Food

| | |
|---|---|
| Dried powder of Example 1 or verproside | 1000 mg |
| Vitamin mixture | optimum amount |
| Vitamin A acetate | 70 μg |
| Vitamin E | 1.0 mg |
| Vitamin B$_1$ | 0.13 mg |
| Vitamin B$_2$ | 0.15 mg |
| Vitamin B6 | 0.5 mg |
| Vitamin B12 | 0.2 μg |
| Vitamin C | 10 mg |
| Biotin | 10 μg |
| Amide nicotinic acid | 1.7 mg |
| Folic acid | 50 μg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above mentioned vitamin and mineral mixture may be varied in many ways. Such variations are not to be regarded as a departure from the spirit and scope of the present invention.

Preparation of Health Beverage

| | |
|---|---|
| Dried powder of Example 1 or verproside | 1000 mg |
| Citric acid | 1000 mg |
| Oligosaccharide | 100 g |
| Apricot concentration | 2 g |
| Taurine | 1 g |
| Distilled water | 900 mL |

Health beverage preparation was prepared by dissolving active component, mixing, stirred at 85° C. for 1 hour, filtered and then filling all the components in 1000 mL ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the extract of *P. longifolium* and the catalpol derivatives isolated therefrom show the suppression of elevated IgE, IL-4 and IL-13 levels and eosinophilia in plasma and BALD, and mucus overproduction in the lung tissues using by OVA-induced asthmatic mouse model. Therefore, it can be used as the therapeutics or functional health food for treating and preventing inflammatory, allergic and asthmatic disease.

We claim:

1. A method of treating asthma disease, comprising administering isolated catalpol derivatives represented by general formula (I) or pharmaceutically acceptable salt thereof as an active ingredient to a subject in need thereof:

(I)

wherein, R is selected from the group consisting of hydrogen, 3,4-dihydroxybenzoyl, 3-hydroxy-4-methozybenzoyl, 4-hydroxybenzoyl, 3,4-dimethoxybenzoyl and cinnamoyl group substituted with 3,4-dihydroxy, 3-hydroxy-4-methoxy, $C_1$-$C_3$ lower alkyl group or $C_1$-$C_3$ lower alkoxy group.

2. The method of claim 1, wherein the isolated catalpol derivative is selected from the group consisting of catalpol, 6-O-3,4-dihydroxybenzoyl catalpol, 6-O-3-hydroxy-4-methoxybenzoly catalpol, 6-O-4-hydroxy-3-methoxybenzoyl, 6-O-3,4-dihydroxycinnamoyl catalpol, 6-O-(3,4-dimethoxybenzoyl) catalpol and 6-O-3-hydroxy-4-methoxycinnamoyl catalpol.

3. The method of claim 1, wherein the isolated catalpol derivative is 6-O-3,4-dihydroxybenzoyl catalpol.

* * * * *